(12) United States Patent
Eskuri (10) Patent No.: US 6,755,847 B2
(45) Date of Patent: Jun. 29, 2004

(54) EMBOLI CAPTURING DEVICE AND METHOD OF MANUFACTURE THEREFOR

(75) Inventor: Alan Eskuri, Hanover, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 270 days.

(21) Appl. No.: 09/972,135

(22) Filed: Oct. 5, 2001

(65) Prior Publication Data

US 2003/0069596 A1 Apr. 10, 2003

(51) Int. Cl.$^7$ .............................................. A61M 29/00
(52) U.S. Cl. ...................................... 606/200; 606/113
(58) Field of Search ............................. 606/200, 113, 606/114, 127

(56) References Cited

U.S. PATENT DOCUMENTS

| | | | |
|---|---|---|---|
| 3,472,230 A | 10/1969 | Fogarty | 128/328 |
| 3,592,186 A | 7/1971 | Oster | 128/2 R |
| 3,683,904 A | 8/1972 | Forster | 128/127 |
| 3,889,657 A | 6/1975 | Baumgarten | 128/2 |
| 3,952,747 A | 4/1976 | Kimmell, Jr. | 128/303 R |
| 3,996,938 A | 12/1976 | Clark, III | 128/348 |
| 4,046,150 A | 9/1977 | Schwartz et al. | 128/328 |
| 4,425,908 A | 1/1984 | Simon | 128/1 |
| 4,447,227 A | 5/1984 | Kotsanis | 604/95 |
| 4,580,568 A | 4/1986 | Gianturco | 128/345 |
| 4,590,938 A | 5/1986 | Segura et al. | 128/328 |
| 4,619,246 A | 10/1986 | Molgaard-Nielsen et al. | 128/1 |
| 4,631,052 A | 12/1986 | Kensey | 604/22 |
| 4,643,184 A | 2/1987 | Mobin-Uddin | 128/303 |
| 4,650,466 A | 3/1987 | Luther | 604/95 |
| 4,662,885 A | 5/1987 | DiPisa, Jr. | 623/12 |
| 4,705,517 A | 11/1987 | DiPisa, Jr. | 623/12 |
| 4,706,671 A | 11/1987 | Weinrib | 128/348.1 |
| 4,723,549 A | 2/1988 | Wholey et al. | 128/344 |
| 4,728,319 A | 3/1988 | Masch | 604/22 |

(List continued on next page.)

FOREIGN PATENT DOCUMENTS

| | | | |
|---|---|---|---|
| DE | 28 21 048 | 7/1980 | A61B/17/22 |
| DE | 34 17 738 | 11/1985 | A61M/1/34 |
| DE | 40 30 998 A1 | 10/1990 | A61F/2/01 |
| DE | 199 16 162 | 10/2000 | |
| EP | 0 200 688 | 11/1986 | A61B/17/22 |
| EP | 0 293 605 A1 | 12/1988 | A61F/2/02 |
| EP | 0 411 118 A1 | 2/1991 | A61M/25/00 |
| EP | 0 427 429 A2 | 5/1991 | A61M/25/10 |
| EP | 0 437 121 B1 | 7/1991 | A61F/2/02 |
| EP | 0 472 334 A1 | 2/1992 | A61F/2/02 |

(List continued on next page.)

OTHER PUBLICATIONS

"Athersclerotic Disease of the Aortic Arch as a Risk Factor of Recurrent Ischemic Stroke," *The New England Journal of Medicine*, pp. 1216–1221 (May 1996).

"Endovascular Grafts, Stents Drive Interventional Radiology Growth," *Cardiovascular Device Update*, 2(3):1–12 (Mar. 1996).

(List continued on next page.)

*Primary Examiner*—Kevin T. Truong
(74) *Attorney, Agent, or Firm*—Crompton, Seager & Tufte LLC (57) ABSTRACT

An intravascular filter device comprising a frame having an open configuration and a closed configuration, the frame comprising a plurality of elongate members each having a proximal end and a distal end, and a proximal region and a distal region and being fixedly connected at the proximal end to each other; and a filter having an open end and a closed end disposed on the frame; wherein the elongate members have a bend distal the proximal region and a helical curve over a substantial length of the distal region when the elongate members are in the open configuration.

8 Claims, 7 Drawing Sheets

U.S. PATENT DOCUMENTS

| | | | | |
|---|---|---|---|---|
| 4,733,665 | A | 3/1988 | Palmaz | 128/343 |
| 4,790,812 | A | 12/1988 | Hawkins, Jr. et al. | 604/22 |
| 4,790,813 | A | 12/1988 | Kensey | 604/22 |
| 4,794,928 | A | 1/1989 | Kletschka | 128/344 |
| 4,794,931 | A | 1/1989 | Yock | 128/660.03 |
| 4,800,882 | A | 1/1989 | Gianturco | 128/343 |
| 4,807,626 | A | 2/1989 | McGirr | 128/328 |
| 4,842,579 | A | 6/1989 | Shiber | 606/22 |
| 4,857,045 | A | 8/1989 | Rydell | 604/22 |
| 4,857,046 | A | 8/1989 | Stevens et al. | 604/22 |
| 4,867,157 | A | 9/1989 | McGurk-Burleson et al. | 128/305 |
| 4,873,978 | A | 10/1989 | Ginsburg | 128/345 |
| 4,898,575 | A | 2/1990 | Fischell et al. | 604/22 |
| 4,907,336 | A | 3/1990 | Gianturco | 29/515 |
| 4,921,478 | A | 5/1990 | Solano et al. | 604/53 |
| 4,921,484 | A | 5/1990 | Hillstead | 604/104 |
| 4,926,858 | A | 5/1990 | Gifford, III et al. | 606/159 |
| 4,950,277 | A | 8/1990 | Farr | 606/159 |
| 4,955,895 | A | 9/1990 | Sugiyama et al. | 606/194 |
| 4,957,482 | A | 9/1990 | Shiber | 604/22 |
| 4,969,891 | A | 11/1990 | Gewertz | 606/200 |
| 4,979,951 | A | 12/1990 | Simpson | 606/159 |
| 4,986,807 | A | 1/1991 | Farr | 604/22 |
| 4,998,539 | A | 3/1991 | Delsanti | 128/898 |
| 5,002,560 | A | 3/1991 | Machold et al. | 606/198 |
| RE33,569 | E | 4/1991 | Gifford, III et al. | 606/159 |
| 5,007,896 | A | 4/1991 | Shiber | 604/22 |
| 5,007,917 | A | 4/1991 | Evans | 606/170 |
| 5,011,488 | A | 4/1991 | Ginsburg | 606/159 |
| 5,019,088 | A | 5/1991 | Farr | 606/159 |
| 5,041,126 | A | 8/1991 | Gianturco | 606/195 |
| 5,053,008 | A | 10/1991 | Bajaj | 604/104 |
| 5,053,044 | A | 10/1991 | Mueller et al. | 606/159 |
| 5,071,407 | A | 12/1991 | Termin et al. | 604/104 |
| 5,071,425 | A | 12/1991 | Gifford, III et al. | 606/159 |
| 5,085,662 | A | 2/1992 | Willard | 606/159 |
| 5,087,265 | A | 2/1992 | Summers | 606/159 |
| 5,100,423 | A | 3/1992 | Fearnot | 606/15 |
| 5,100,424 | A | 3/1992 | Jang et al. | 606/159 |
| 5,100,425 | A | 3/1992 | Fischell et al. | 606/159 |
| 5,102,415 | A | 4/1992 | Guenther et al. | 606/159 |
| 5,104,399 | A | 4/1992 | Lazarus | 623/1 |
| 5,108,419 | A | 4/1992 | Reger et al. | 606/200 |
| 5,133,733 | A | 7/1992 | Rasmussen et al. | 606/200 |
| 5,135,531 | A | 8/1992 | Shiber | 606/159 |
| 5,152,771 | A | 10/1992 | Sabbaghian et al. | 606/159 |
| 5,152,777 | A | 10/1992 | Goldberg et al. | 606/200 |
| 5,160,342 | A | 11/1992 | Reger et al. | 606/200 |
| 5,171,233 | A | 12/1992 | Amplatz et al. | 604/281 |
| 5,190,546 | A | 3/1993 | Jervis | 606/78 |
| 5,195,955 | A | 3/1993 | Don Michael | 604/22 |
| 5,224,953 | A | 7/1993 | Morgentaler | 606/192 |
| 5,306,286 | A | 4/1994 | Stack et al. | 606/198 |
| 5,314,444 | A | 5/1994 | Gianturco | 606/195 |
| 5,314,472 | A | 5/1994 | Fontaine | 623/12 |
| 5,318,576 | A | 6/1994 | Plassche, Jr. et al. | 606/159 |
| 5,329,942 | A | 7/1994 | Gunther et al. | 128/898 |
| 5,330,484 | A | 7/1994 | Gunther | 606/128 |
| 5,330,500 | A | 7/1994 | Song | 606/198 |
| 5,350,398 | A | 9/1994 | Pavcnik et al. | 606/200 |
| 5,354,310 | A | 10/1994 | Garnic et al. | 606/198 |
| 5,356,423 | A | 10/1994 | Tihon et al. | 606/194 |
| 5,366,464 | A | 11/1994 | Belknap | 606/159 |
| 5,366,473 | A | 11/1994 | Winston et al. | 606/198 |
| 5,370,657 | A | 12/1994 | Irie | 606/200 |
| 5,370,683 | A | 12/1994 | Fontaine | 623/1 |
| 5,376,100 | A | 12/1994 | Lefebvre | 606/180 |
| 5,383,887 | A | 1/1995 | Nadal | 606/200 |
| 5,383,892 | A | 1/1995 | Cardon et al. | 606/198 |
| 5,383,926 | A | 1/1995 | Lock et al. | 623/1 |
| 5,387,235 | A | 2/1995 | Chuter | 623/1 |
| 5,395,349 | A | 3/1995 | Quiachon et al. | 604/248 |
| 5,397,345 | A | 3/1995 | Lazarus | 623/1 |
| 5,405,377 | A | 4/1995 | Cragg | 623/1 |
| 5,409,454 | A | 4/1995 | Fischell et al. | 604/22 |
| 5,415,630 | A | 5/1995 | Gory et al. | 604/53 |
| 5,419,774 | A | 5/1995 | Willard et al. | 604/22 |
| 5,421,832 | A | 6/1995 | Lefebvre | 604/53 |
| 5,423,742 | A | 6/1995 | Theron | 604/28 |
| 5,423,885 | A | 6/1995 | Williams | 623/1 |
| 5,425,765 | A | 6/1995 | Tiefenbrun et al. | 623/12 |
| 5,443,498 | A | 8/1995 | Fontaine | 623/1 |
| 5,449,372 | A | 9/1995 | Schmaltz et al. | 606/198 |
| 4,842,579 | A | 10/1995 | Shiber | 604/22 |
| 5,456,667 | A | 10/1995 | Ham et al. | 604/107 |
| 5,462,529 | A | 10/1995 | Simpson et al. | 604/101 |
| 5,476,104 | A | 12/1995 | Sheahon | 128/757 |
| 5,484,418 | A | 1/1996 | Quiachon et al. | 604/167 |
| 5,507,767 | A | 4/1996 | Maeda et al. | 606/198 |
| 5,512,044 | A | 4/1996 | Duer | 604/22 |
| 5,527,354 | A | 6/1996 | Fontaine et al. | 623/1 |
| 5,536,242 | A | 7/1996 | Willard et al. | 604/30 |
| 5,540,707 | A | 7/1996 | Ressemann et al. | 606/159 |
| 5,549,626 | A | 8/1996 | Miller et al. | 606/200 |
| 5,562,724 | A | 10/1996 | Vowerk et al. | 623/1 |
| 5,569,274 | A | 10/1996 | Rapacki et al. | 606/158 |
| 5,569,275 | A | 10/1996 | Kotula et al. | 606/159 |
| 5,634,897 | A | 6/1997 | Dance et al. | 604/35 |
| 5,658,296 | A | 8/1997 | Bates et al. | 606/127 |
| 5,662,671 | A | 9/1997 | Barbut et al. | 606/170 |
| 5,669,933 | A | 9/1997 | Simon et al. | 600/200 |
| 5,695,519 | A | 12/1997 | Summers et al. | 606/200 |
| 5,709,704 | A | 1/1998 | Nott et al. | 606/200 |
| 5,720,764 | A | 2/1998 | Naderlinger | 606/200 |
| 5,728,066 | A | 3/1998 | Daneshvar | 604/96 |
| 5,746,758 | A | 5/1998 | Nordgren et al. | 606/159 |
| 5,749,848 | A | 5/1998 | Jang et al. | 604/53 |
| 5,769,816 | A | 6/1998 | Barbut et al. | 604/96 |
| 5,779,716 | A | 7/1998 | Cano et al. | 606/114 |
| 5,792,157 | A | 8/1998 | Mische et al. | |
| 5,792,300 | A | 8/1998 | Inderbitzen et al. | 156/244.13 |
| 5,795,322 | A | 8/1998 | Boudewijn | 604/22 |
| 5,797,952 | A | 8/1998 | Klein | 606/198 |
| 5,800,457 | A | 9/1998 | Gelbfish | 606/200 |
| 5,800,525 | A | 9/1998 | Bachinski et al. | 623/1 |
| 5,810,874 | A | 9/1998 | Lefebvre | 606/200 |
| 5,814,064 | A | 9/1998 | Daniel et al. | 606/200 |
| 5,817,102 | A | 10/1998 | Johnson et al. | 606/108 |
| 5,827,324 | A | 10/1998 | Cassell et al. | 606/200 |
| 5,833,644 | A | 11/1998 | Zadno-Azizi et al. | 604/52 |
| 5,833,650 | A | 11/1998 | Imran | 604/53 |
| 5,846,260 | A | 12/1998 | Maahs | 606/200 |
| 5,848,964 | A | 12/1998 | Samuels | 600/200 |
| 5,876,367 | A | 3/1999 | Kaganov et al. | 604/8 |
| 5,893,867 | A | 4/1999 | Bagaoisan et al. | 606/198 |
| 5,895,399 | A | 4/1999 | Barbut et al. | 606/159 |
| 5,902,263 | A | 5/1999 | Patterson et al. | 604/22 |
| 5,906,618 | A | 5/1999 | Larson, III | 606/108 |
| 5,908,435 | A | 6/1999 | Samuels | 606/200 |
| 5,910,154 | A | 6/1999 | Tsugita et al. | 606/200 |
| 5,911,734 | A | 6/1999 | Tsugita et al. | 606/200 |
| 5,916,193 | A | 6/1999 | Stevens et al. | 604/53 |
| 5,925,016 | A | 7/1999 | Chornenky et al. | 604/96 |
| 5,925,060 | A | 7/1999 | Forber | 606/191 |
| 5,925,062 | A | 7/1999 | Purdy | 606/200 |
| 5,925,063 | A | 7/1999 | Khosravi | 606/200 |
| 5,928,203 | A | 7/1999 | Davey et al. | 604/247 |
| 5,928,218 | A | 7/1999 | Gelbfish | 604/540 |
| 5,934,284 | A | 8/1999 | Plaia et al. | 128/898 |
| 5,935,139 | A | 8/1999 | Bates | 606/159 |

| | | | |
|---|---|---|---|
| 5,938,645 A | 8/1999 | Gordon | 604/264 |
| 5,941,869 A | 8/1999 | Patterson et al. | 604/508 |
| 5,941,896 A | 8/1999 | Kerr | 606/200 |
| 5,947,995 A | 9/1999 | Samuels | 606/200 |
| 5,951,585 A | 9/1999 | Cathcart et al. | 606/198 |
| 5,954,745 A | 9/1999 | Gertler et al. | 606/200 |
| 5,976,172 A | 11/1999 | Homsma et al. | 606/200 |
| 5,980,555 A | 11/1999 | Barbut et al. | |
| 5,989,210 A | 11/1999 | Morris et al. | 604/22 |
| 5,989,271 A | 11/1999 | Bonnette et al. | 606/159 |
| 5,989,281 A | 11/1999 | Barbut et al. | 606/200 |
| 5,993,469 A | 11/1999 | McKenzie et al. | 606/159 |
| 5,997,557 A | 12/1999 | Barbut et al. | 606/159 |
| 6,001,118 A | 12/1999 | Daniel et al. | 606/200 |
| 6,007,557 A | 12/1999 | Ambrisco et al. | 606/200 |
| 6,010,522 A | 1/2000 | Barbut et al. | 606/200 |
| 6,013,085 A | 1/2000 | Howard | 606/108 |
| 6,027,520 A | 2/2000 | Tsugita et al. | 606/200 |
| 6,042,598 A | 3/2000 | Tsugita et al. | |
| 6,051,014 A | 4/2000 | Jang | 606/200 |
| 6,051,015 A | 4/2000 | Maahs | |
| 6,053,932 A | 4/2000 | Daniel et al. | 606/200 |
| 6,059,814 A | 5/2000 | Ladd | 606/200 |
| 6,066,149 A | 5/2000 | Samson et al. | |
| 6,068,645 A | 5/2000 | Tu | 606/200 |
| 6,086,605 A | 7/2000 | Barbut et al. | 606/200 |
| 6,117,154 A | 9/2000 | Barbut et al. | |
| 6,129,739 A | 10/2000 | Khosravi | 606/200 |
| 6,136,016 A | 10/2000 | Barbut et al. | |
| 6,142,987 A | 11/2000 | Tsugita | 604/500 |
| 6,152,946 A | 11/2000 | Broome et al. | 606/200 |
| 6,165,200 A | 12/2000 | Tsugita et al. | 606/200 |
| 6,168,579 B1 | 1/2001 | Tsugita | 604/96.01 |
| 6,171,327 B1 | 1/2001 | Daniel et al. | 606/200 |
| 6,171,328 B1 | 1/2001 | Addis | |
| 6,179,851 B1 | 1/2001 | Barbut et al. | 606/159 |
| 6,179,859 B1 | 1/2001 | Bates et al. | 606/200 |
| 6,179,861 B1 | 1/2001 | Khosravi et al. | 606/200 |
| 6,203,561 B1 | 3/2001 | Ramee et al. | 606/200 |
| 6,206,868 B1 | 3/2001 | Parodi | |
| 6,214,026 B1 | 4/2001 | Lepak et al. | 606/200 |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,344,049 B1 | 2/2002 | Levinson et al. | |
| 6,468,291 B2 * | 10/2002 | Bates et al. | 606/200 |
| 6,485,501 B1 * | 11/2002 | Green | 606/200 |
| 6,540,722 B1 * | 4/2003 | Boyle et al. | 606/200 |
| 6,562,058 B2 * | 5/2003 | Seguin et al. | 606/200 |

FOREIGN PATENT DOCUMENTS

| | | | | |
|---|---|---|---|---|
| EP | 0 472 368 A2 | 2/1992 | | A61B/17/22 |
| EP | 0 533 511 A1 | 3/1993 | | A61M/29/02 |
| EP | 0 655 228 A1 | 11/1994 | | A61F/2/02 |
| EP | 0 686 379 A2 | 6/1995 | | A61F/2/06 |
| EP | 0 696 447 A2 | 2/1996 | | A61F/2/06 |
| EP | 0 737 450 A1 | 10/1996 | | A61F/2/01 |
| EP | 0 743 046 A1 | 11/1996 | | A61F/2/01 |
| EP | 0 759 287 A1 | 2/1997 | | A61F/2/01 |
| EP | 0 771 549 A2 | 5/1997 | | A61F/2/01 |
| EP | 0 784 988 A1 | 7/1997 | | A61M/5/165 |
| EP | 0 852 132 A1 | 7/1998 | | A61F/2/01 |
| EP | 1 123 688 A | 8/2001 | | |
| EP | 1 127 556 A2 | 8/2001 | | |
| FR | 2 580 504 | 10/1986 | | A61M/1/00 |
| FR | 2 643 250 A1 | 8/1990 | | A61B/17/00 |
| FR | 2 666 980 | 3/1992 | | A61F/2/02 |
| FR | 2 694 687 | 8/1992 | | |
| FR | 2 768 326 A1 | 3/1999 | | A61F/92/01 |
| GB | 2 020 557 B | 1/1983 | | A61B/17/50 |
| JP | 8-187294 A | 7/1996 | | A61M/29/00 |
| RU | 764684 | 9/1980 | | A61M/25/00 |
| WO | WO 92/03097 | 3/1992 | | A61B/17/00 |
| WO | WO 94/14389 | 7/1994 | | A61F/2/02 |
| WO | WO 94/24946 | 11/1994 | | A61B/17/22 |
| WO | WO 96/01591 | 1/1996 | | A61B/17/22 |
| WO | WO 96/10375 | 4/1996 | | A61F/2/06 |
| WO | WO 96/19941 | 7/1996 | | A61B/17/00 |
| WO | WO 96/23441 | 8/1996 | | A61B/5/00 |
| WO | WO 96/33677 | 10/1996 | | A61F/11/00 |
| WO | WO 97/17100 | 5/1997 | | A61M/29/00 |
| WO | WO 97/27808 | 8/1997 | | A61B/17/22 |
| WO | WO 97/42879 | 11/1997 | | A61B/17/00 |
| WO | WO 98/02084 | 1/1998 | | |
| WO | WO 98/02112 | 1/1998 | | A61F/2/01 |
| WO | WO 98/23322 | 6/1998 | | A61M/29/00 |
| WO | WO 98/33443 | 8/1998 | | A61B/17/22 |
| WO | WO 98/34673 | 8/1998 | | A61M/31/00 |
| WO | WO 98/36786 | 8/1998 | | A61M/5/32 |
| WO | WO 98/38920 | 9/1998 | | A61B/17/00 |
| WO | WO 98/38929 | 9/1998 | | A61B/17/22 |
| WO | WO 98/39046 | 9/1998 | | A61M/25/00 |
| WO | WO 98/39053 | 9/1998 | | A61M/29/00 |
| WO | WO 98/46297 | 10/1998 | | A61M/29/00 |
| WO | WO 98/47447 | 10/1998 | | A61F/2/06 |
| WO | WO 98/49952 | 11/1998 | | A61B/17/32 |
| WO | WO 98/50103 | 11/1998 | | A61M/29/00 |
| WO | WO 98/51237 | 11/1998 | | A61F/2/01 |
| WO | WO 98/55175 | 12/1998 | | A61M/29/00 |
| WO | WO 99/09895 | 3/1999 | | A61B/17/12 |
| WO | WO 99/22673 | 5/1999 | | A61F/2/01 |
| WO | WO 99/23976 | 5/1999 | | A61F/2/01 |
| WO | WO 99/25252 | 5/1999 | | A61B/17/00 |
| WO | WO 99/30766 | 6/1999 | | A61M/29/00 |
| WO | 0 934 729 | 8/1999 | | A61B/17/22 |
| WO | WO 99/40964 | 8/1999 | | A61M/29/02 |
| WO | WO 99/42059 | 8/1999 | | A61F/2/06 |
| WO | WO 99 44510 A | 9/1999 | | |
| WO | WO 99/44510 | 9/1999 | | A61B/17/00 |
| WO | WO 99/44542 | 9/1999 | | A61F/2/06 |
| WO | WO 99/55236 | 11/1999 | | A61B/17/00 |
| WO | WO 99/58068 | 11/1999 | | A61B/17/22 |
| WO | WO 00/07521 | 2/2000 | | |
| WO | WO 00/07655 | 2/2000 | | A61M/29/00 |
| WO | WO 00/09054 | 2/2000 | | A61F/7/12 |
| WO | WO 00/16705 | 3/2000 | | A61B/17/22 |
| WO | WO 00/49970 | 8/2000 | | A61F/2/01 |
| WO | WO 00/53120 | 9/2000 | | |
| WO | WO 00/67664 | 11/2000 | | |
| WO | WO 00/67665 | 11/2000 | | |
| WO | WO 00/67666 | 11/2000 | | |
| WO | WO 00/67668 | 11/2000 | | |
| WO | WO 00/67669 | 11/2000 | | |
| WO | WO 01/05462 | 1/2001 | | |
| WO | WO 01/08595 | 2/2001 | | |

| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/45592 A1 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Protruding Atheromas in the Thoracic Aortic and Systemic Embolization," pp. 423–427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger", *AJR*, 141:601–604 (Sep. 1983).
Cragg, Andrew et al., "Nonsurgical Placement of Arterial Endoprosthesis: A New Technique Using Nitinol Wire," *AJR*, pp. 261–263 (Apr. 1983).
Diethrich et al., "Percutaneous Techniques for Endoluminal Carotid Interventions," *J. Endovasc. Surg.*, 3:182–202 (1996).
Fadali, A. Moneim, "A filtering device for the prevention of particulate embolization during the course of cardiac surgery," *Surgery*, 64(3):634–639 (Sep. 1968).
Haissaguerre et al., "Spontaneous Initiation of Atrial Fibrillation by Ectopic Beats Originating in the Pulmonary Veins," *The New England Journal of Medicine*, 339(10):659–666 (Sep. 1988).
Jordan, Jr. et al., "Microemboli Detected by Transcranial Doppler Monitoring . . . ," *Cardiovascular Surgery*, 7(1)33–38 (Jan. 1999).
Lesh, "Can Catheter Ablation Cure Atrial Fibrillation?" *ACC Current Journal Review*, pp. 38–40 (Sep./Oct. 1997).
Lund et al., "Long–Term Patentcy of Ductus Arteriosus After Balloon Dilation: an Experimental Study," *Laboratory Investigation*, 69(4):772–774 (Apr. 1984).
Marache et al., "Percutaneous Transluminal Venous Angioplasty . . . ," *American Heart Journal*, 125(2 Pt 1):362–366 (Feb. 1993).
Mazur et al., "Directional Atherectomy with the Omnicath™: A Unique New Catheter System," *Catheterization and Cardiovascular Diagnosis*, 31:17–84 (1994).
Moussa, MD, Issaam "Stents Don't Require Systemic Anticoagulation . . . But the Technique (and Results) Must be Optimal," *Journal of Invasive Cardiol.*, 8(E):3E–7E, (1996).
Nakanishi et al., "Catheter Intervention to Venous System Using Expandable Metallic Stents," Rinsho Kyobu Geka, 14(2):English Abstract Only (Apr. 1994).
Onal et al., "Primary Stenting for Complex Atherosclerotic Plaques in Aortic and Iliac Stenoses," *Cardiovascular & Interventional Radiology*, 21(5):386–392 (1998).
Theron et al., "New Triple Coaxial Catheter System for Carotid Angioplasty with Cerebral Protection," *American Journal of Neuroradiology*, 11:869–874 (1990).
Tunick et al., "Protruding atherosclerotic plaque in the aortic archo f patients with systemic embolization: A new finding seen by transesophageal echocardiography," *American Heart Journal* 120(3):658–660 (Sep. 1990).
Waksman et al., "Distal Embolization is Common After Directional Atherectomy . . . ," *American Heart Journal*, 129(3):430–435 (1995).
Wholey, Mark H. et al., PTA and Stents in the Treatment of Extracranial Circulation, *The Journal of Invasive Cardiology*, 8(E):25E–30E (1996).

* cited by examiner

EMBOLI CAPTURING DEVICE AND METHOD OF MANUFACTURE THEREFOR

FIELD OF THE INVENTION

This invention relates generally to intravascular medical devices. More particularly it relates to a device used for capturing emboli in a fluid vessel during a variety of intravascular medical procedures and a method of manufacture for that device.

BACKGROUND OF THE INVENTION

There are a number of intravascular procedures where emboli may be created in the vasculature. It may be desirable to capture these emboli before they flow downstream.

SUMMARY OF THE INVENTION

Embodiments of the invention pertain to a device for capturing emboli in fluid flowing in a body vessel lumen and a method of manufacturing the device. Certain embodiments of the invention more particularly pertain to a frame and a filter material portion of the emboli capturing system. In certain embodiments the frame comprises a plurality of proximally fixed elongate members attached to a collar which are expandable into a generally helical pattern. This generally helical pattern of elongate members is configured to open the mouth of the filter to a generally circular shape which contacts the walls of the body vessel lumen to channel the fluid through the filter.

The frame and collar embodiment may be manufactured from a tube of a suitable material such as Nitinol by cutting a number of slits down a substantial portion of the tube and shape setting the elongate members resulting from the slits. This method of manufacture, where the elongate members and the collar are formed from a single tube, provides a ready means of orienting the elongate members with respect to each other and may easily be adapted to frame and filter devices having a different strut configuration.

DETAILED DESCRIPTION

The following description should be read with reference to the drawings wherein like reference numerals indicate like elements throughout the several drawings. The detailed description and drawings represent select embodiments and are not intended to be limiting.

Figure 1:
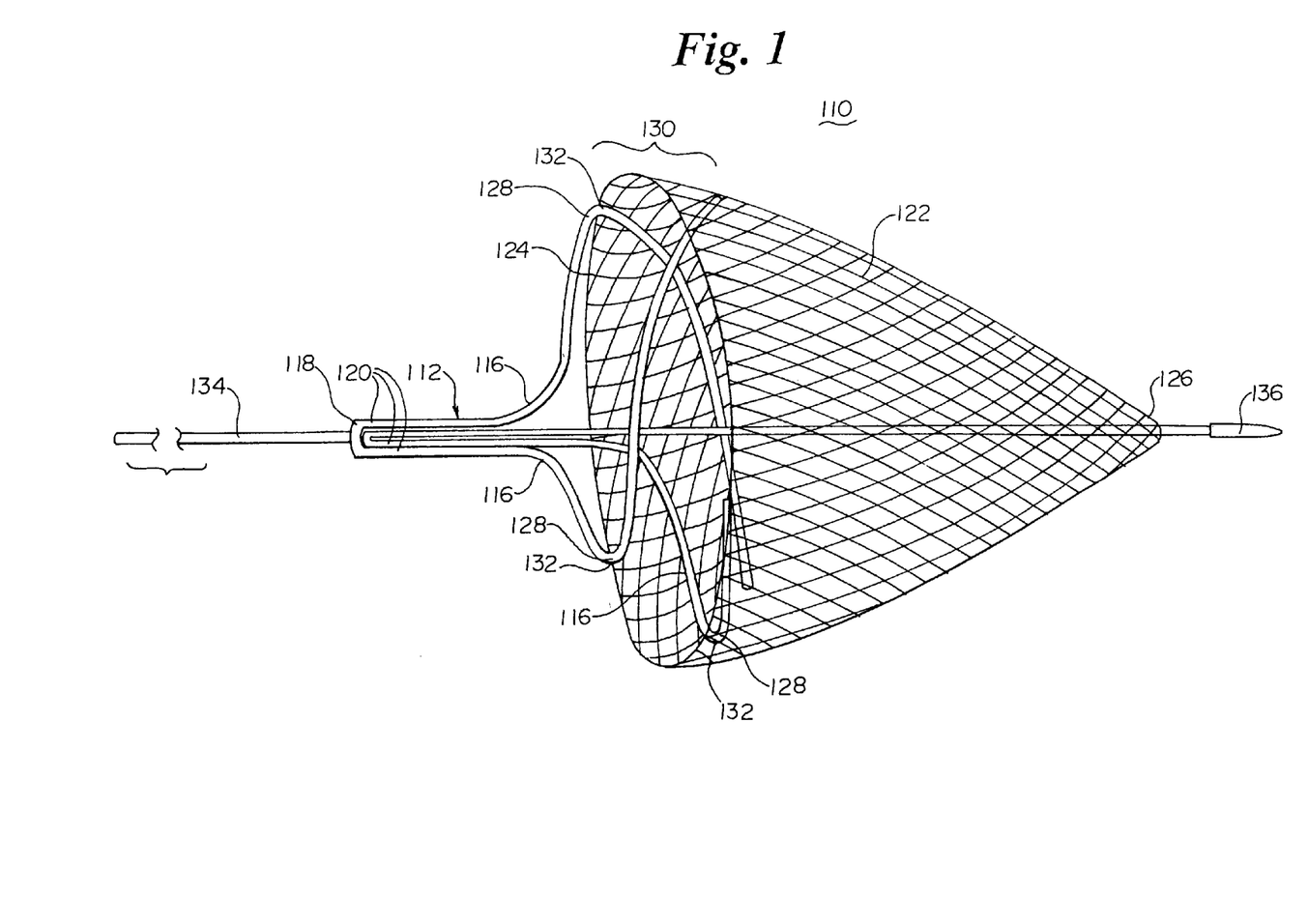
FIG. 1 shows an isometric view of emboli capturing device 110 in an expanded state according to the invention.

FIG. 1 is an isometric view illustrating an emboli capturing device 110 constructed in accordance with the principles of the invention. A frame 112 includes a plurality of elongate members 116 and a collar 118. The plurality of elongate members 116 is fixedly connected at their proximal ends 120 to each other and may be attached to a collar 118. Plurality of elongate members 116 is configured so that elongate members 116 will bend outward proximal a distal region 130 of elongate members 116 and bend generally helically at distal region 130. Elongate members 116 may also bend generally in a spiral shape proximal distal region 130 of elongate members 116. The elongate members 116 may have a region 132 between the outward bending portion and the generally helical portion whose axis will be generally parallel to the axis running through the center of emboli capturing device 110 both when elongate members 116 are in the expanded position as shown in FIG. 1 and the compressed position as shown in FIG. 2.

A filter material 122 is disposed such that an open end 124 of filter material 122 is proximal a closed end 126 of filter material 122. Plurality of elongate members 116 are attached to filter material 122 at points 128 proximate open end 124 of filter material 122 and extend within filter material 122. Every elongate member 116 may be attached to filter material 122 at points 128 or optionally a lesser number of elongate members 116 may be attached to filter material 122 at points 128. Points 128 are generally located towards the proximal end of distal region 130 and may be located at region 132 to provide an attachment location where filter material 122 is subjected to a minimum of rotational stress.

Emboli capturing device 110 may be disposed on a wire 134 and may be connected to wire 134 at proximal ends 120 of elongate members 116. Filter material 122 may be attached to wire 134 at closed end 126 or may be slideably disposed on wire 134 at closed end 126 of filter material. An atraumatic tip 136 may be attached to the distal end of wire 134.

Figure 2:
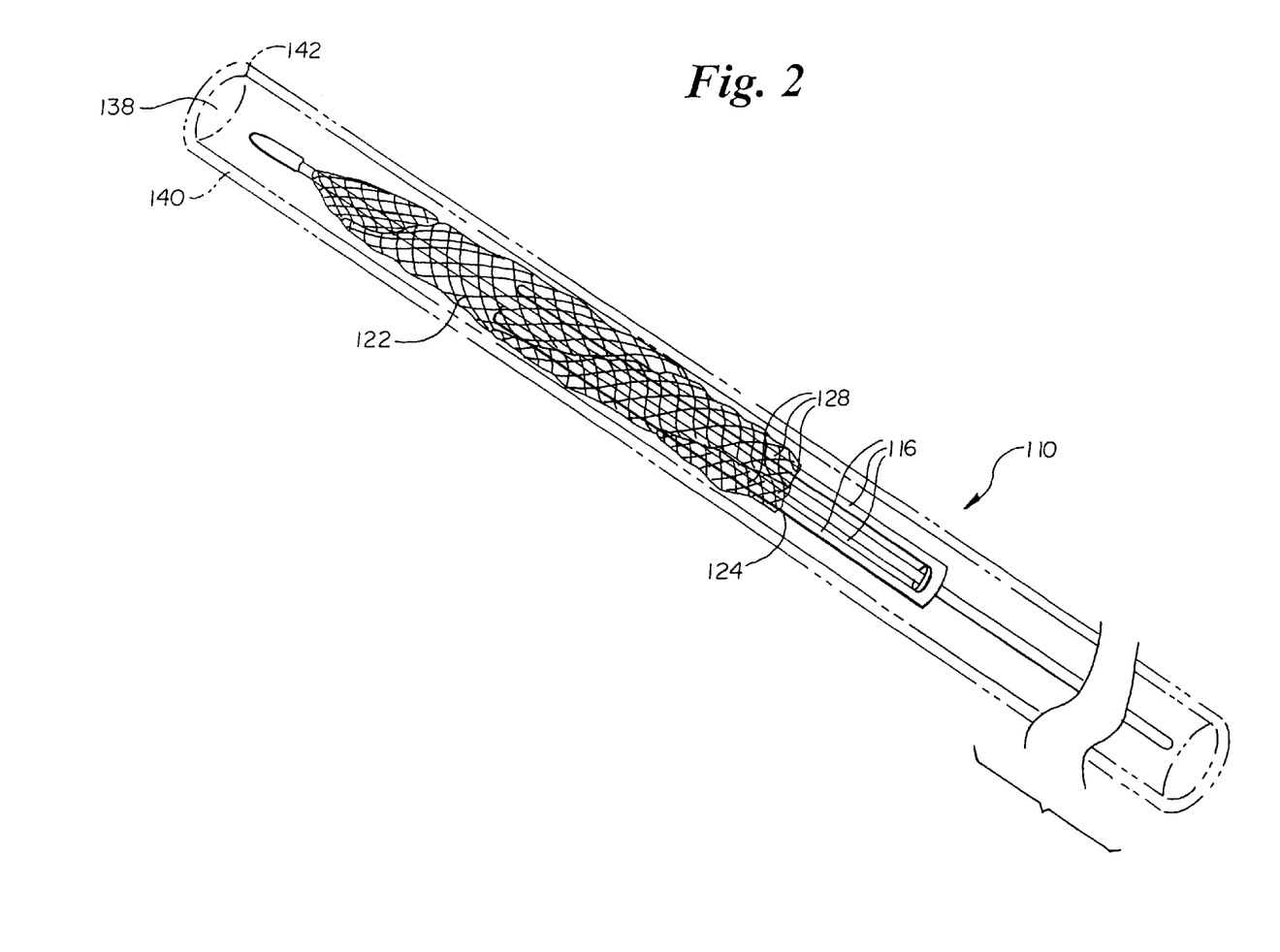
FIG. 2 shows an isometric view of emboli capturing device 110 in a contracted state according to the invention.

Emboli capturing device 110 may be compressed within a lumen 138 of a catheter sheath 140 as depicted in FIG. 2. As catheter sheath 140 is slid distally over emboli capturing device 110, a distal lip 142 of catheter sheath 140 forces elongate members 116 inward. As elongate members 116 are forced inward, points 128 proximate open end 124 of filter material 122, which is attached to elongate members 116 at points 128, are forced together, collapsing filter material 122 and allowing it to be drawn into catheter sheath 140. When emboli capturing device 110 is compressed in catheter sheath 140, the plurality of elongate members 116 is disposed longitudinally generally parallel to the axis of catheter sheath 140 and filter material 122 collapses from its expanded shape.

If elongate members 116 have a generally spiral shape bend as described above, when elongate members are collapsing, points 128 will rotate and twist filter material 122 during the collapsing process.

Figure 3:
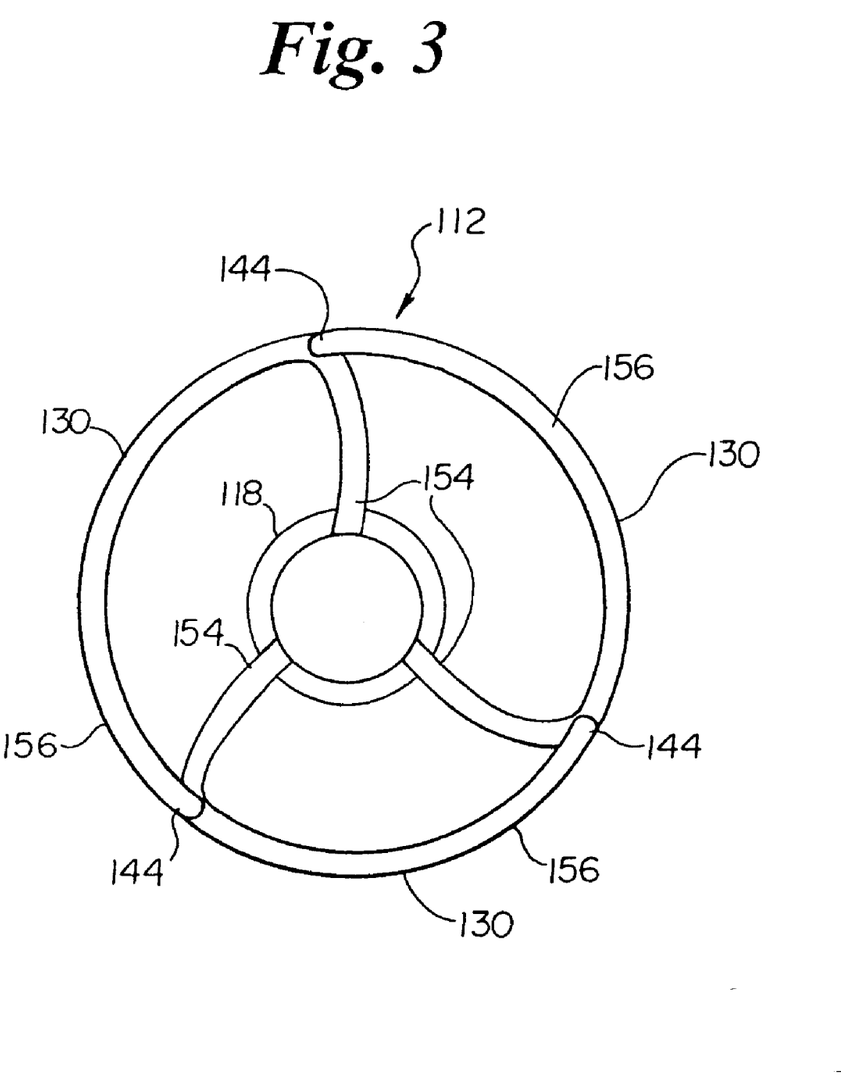
FIG. 3 shows an end view of frame 112 used in emboli capturing device 110 according to the invention.

FIG. 3 shows an end view of frame 112 of emboli capturing device 110 in its expanded position. Elongate members 116 have a bend 154 proximal distal region 130 and a generally helical shape 156 at distal region 130 of elongate members 116. When frame 112 is in the expanded position, the plurality of elongate members 116 may be configured so that distal ends 144 of elongate members 116 overlap the adjacent elongate member 116 such that the perimeter of open end 124 of filter material 122 is given a generally circular shape. This configuration allows filter material 122 to efficiently capture the fluid flow.

Elongate members 116 and collar 118 may be made of any resilient flexible material such as Nitinol, stainless steel, polymer or other suitable material. Bends 154 and generally helical shapes 156 may be molded or shape set into the material.

Filter material 116 may be made of a number of materials well known in the art such as polyethylene meshes manufactured by Saati Tech and Tetko, Inc. An appropriate material may allow blood cells to pass freely through while capturing emboli of a targeted size. Filter material 116 is depicted in the drawings as conical, but many shapes which have an open end and a closed end are suitable for use in embodiments of the invention. Filter material 116 may be disposed on Frame 112 such that open end 124 is either proximal or distal closed end 126, as discussed with respect to FIG. 4 below.

Wire 134 may be manufactured from a number of materials commonly used in the art to make guidewires and other wires used in the medical device industry such as stainless steel or Nitinol.

The manufacture of catheters suitable for use as catheter sheath 140 is well known in the art. Catheter sheath 140 may be made from a substantially flexible material such as polyethylene, polymer block amides, nylon, or other suitable material.

Emboli capturing device 110 may be used downstream of a treatment site in the following manner. Emboli capturing device 110 may be inserted into a deployment sheath. Elongate members 116 and filter material 122 may generally be tightly compressed and the deployment sheath may generally be sized to have the minimum outer diameter sufficient to contain emboli capturing device 110. The deployment sheath may then be inserted into a body vessel lumen (not shown), generally percutaneously, and advanced to a location downstream of the treatment site. The deployment sheath may then be withdrawn, allowing elongate members 116 and filter material 122 to reach their expanded state. The treatment site therapy may then be performed. The treatment site therapy may be a variety of intravascular procedures including, for example, balloon angioplasty, stent insertion, or release of a therapeutic agent. If the treatment site therapy creates any emboli, the fluid flowing past the treatment site will flow through the filter material, allowing the emboli capturing device to capture the emboli. When retrieval of the device is desired a retrieval sheath may be distally advanced over the emboli capturing device, collapsing the device as described above. The retrieval sheath may generally have a larger inner diameter that the deployment sheath to accommodate any emboli that may be captured by the device. The retrieval sheath may then be removed proximally from the body vessel lumen together with the emboli capturing device.

Figure 4:
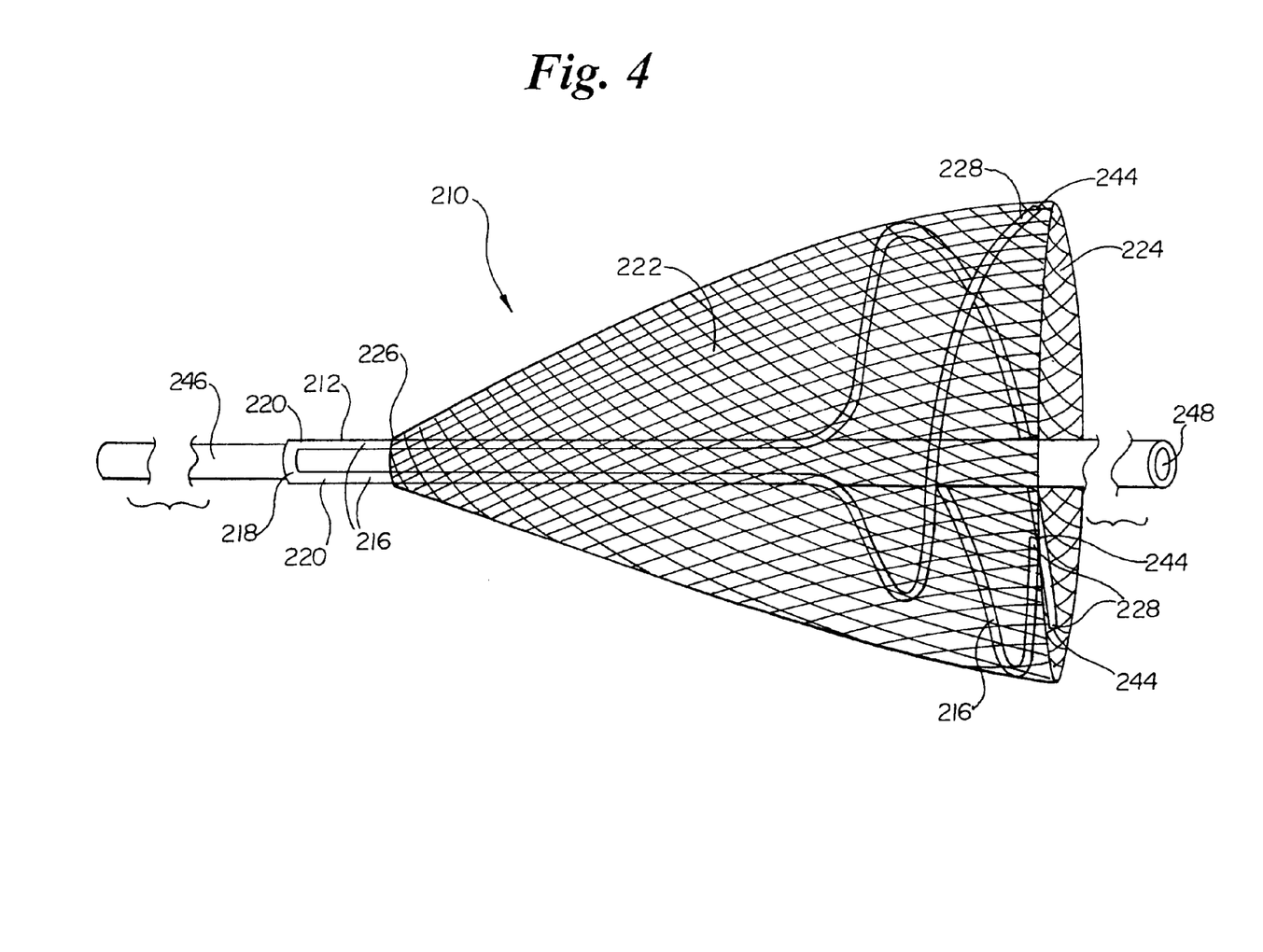
FIG. 4 shows an isometric view of emboli capturing device 210 according to the invention.

FIG. 4 shows an isometric view of an emboli capturing device 210 in accordance with the invention. Like emboli capturing device 110, a frame 212 comprises a plurality of elongate members 216 connected at their proximal ends 220 to each other. Elongate members 216 may also be connected at their proximal ends to a collar 218. Frame 212 may have generally the same shape as frame 112. In emboli capturing device 210 however, filter material 222 is positioned such that open end 224 of filter material 222 is distal closed end 226 of filter material 222. Filter material 222 is attached to elongate members 216 proximate open end 224 of filter material 222 at points 228. Points 228 may be located proximate distal ends 244 of elongate members 216. Filter material 222 may be attached to or slideably disposed on elongate members 216 at closed end 226 of filter material 222.

Emboli capturing device 210 may be disposed on a catheter 246. Other devices such as an angioplasty balloon (not shown) may be attached to catheter 146 or deployed through a lumen 248 of catheter 246. Closed end 226 of filter material 222 may be attached to catheter 246 and collar 218 may be slideably disposed on catheter 246. Emboli capturing device 210 may be deployed and retrieved in a manner similar to that of the first embodiment.

Emboli capturing device 110 may be better adapted for use when the fluid in the body vessel lumen flows distally from the treatment site. Emboli capturing device 110 may be on a guidewire 134 and has open end 124 of filter material 122 proximal closed end 126 of filter material 122. Emboli capturing device 210 may be better adapted for use when the fluid in the body vessel lumen flows proximally from the treatment site. Emboli capturing device 210 may be on a catheter 246 through which guidewires and treatment site devices such as angioplasty balloons may be used, and has open end 224 of filter material 222 distal closed end 226 of filter material 222.

Figure 5:
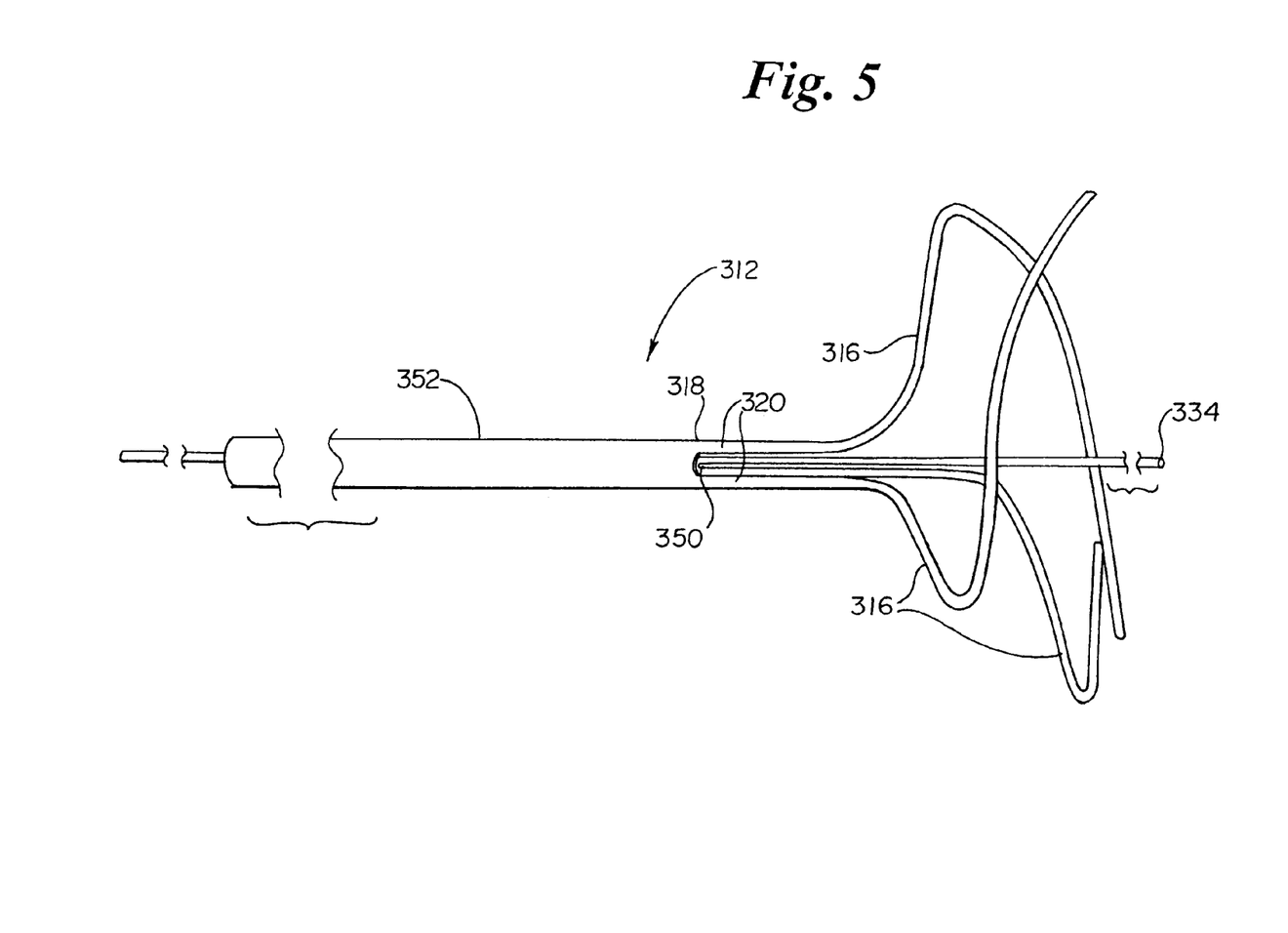
FIG. 5 shows an isometric view of frame embodiment 312 according to the invention.

FIG. 5 is an isometric view of a frame 312 according to the invention. Frame 312 may be used with either emboli capturing device 110 or 210. Frame 312 has elongate members 316 connected to each other at proximal end 320 and attached to a collar 318. Collar 318 extends proximally to form a longitudinal catheter like member 352 creating a lumen 350. If frame 312 is used with emboli capturing device 110 in lieu of frame 112, a wire 334 may be extended through lumen 350. Alternatively, member 352 may serve in lieu of proximal portion of wire 334 and one or more elongate members 316 may be made to extend generally parallel to the axis of the emboli capturing device in both the expanded and the contracted state to serve in lieu of the distal portion of wire 334. If frame 312 is used with emboli capturing device 210 in lieu of frame 212, member 352 may serve in place of catheter 240. Frame 312 is suited to manufacturing collar 318 and member 350 from one tube although collar 318 and member 350 may also be made separately and subsequently joined.

Figure 6:
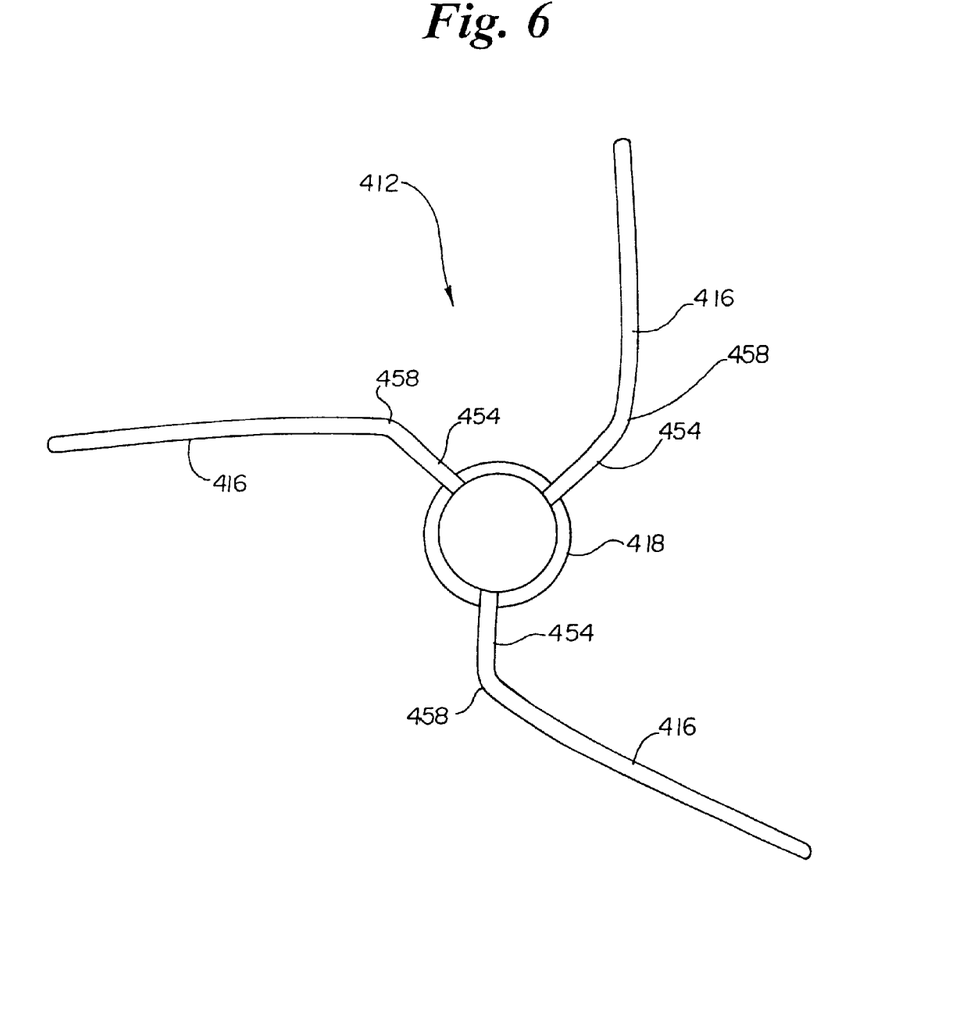
FIG. 6 shows an isometric view of frame embodiment 412 according to the invention.

FIG. 6 is an end view of an alternate frame 412 shown without filter material. Frame 412 comprises collar 418 and elongate members 416. In this embodiment elongate member 416 have a bend 454 and a second bend 458. This embodiment uses the constraint of a filter material 422 (not shown in this figure) and a vessel lumen wall (not shown) to form a distal region 430 of elongate members 416 into a generally helical shape.

Figure 7:
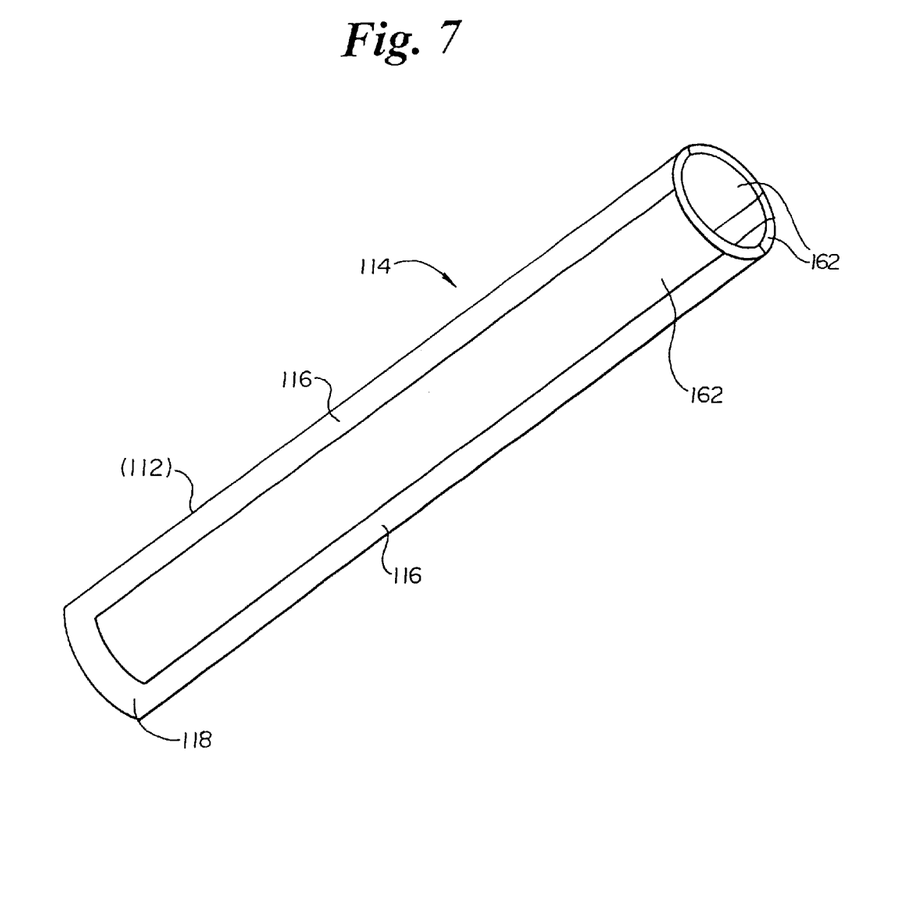
FIG. 7 shows a tube 114 from which frame 112 may be manufactured.

FIG. 7 is an illustration of a tube 114 which may be formed into frame 112 for use in emboli capturing device 110. The material in slots 162 may be removed to form longitudinal members 116 and collar 118. The material in slots 162 may be removed such that slots 162 have radial walls, parallel walls or such that elongate members 116 have parallel walls. The desired configuration may then be shape-set into elongate members 116. Variations are contemplated where different numbers of elongate members 116 are formed and where elongate members 116 have a variety of cross-sectional profiles. This method of manufacture where elongate members 116 and collar 118 are manufactured from a single tube 114 allows precise positioning of elongate members 116. This method of manufacture may easily be adapted for use with many frame configurations, including other frame configurations disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method of manufacture of an intravascular filter device comprising the steps of:

provi­ding a tube, the tube having an outer diameter and an inner diameter, an axis running through the center of the tube, and a proximal end and a distal end;

cutting slots in the tube extending from the outer diameter to the inner diameter and from the distal end to a point proximate the proximal end, such that the slots create elongate members having a distal region and a proximal region fixedly attached by a ring of tube material at the proximal end of the tube;

shape-setting the elongate members to expand from a first position to a second position, in the second position the elongate members extending generally away from and around the axis of the tube to form a generally circulative mouth; and disposing a filter material on the distal end.

2. The method of manufacture of claim 1, wherein the slots have radial walls.

3. The method of manufacture of claim 1, wherein the slots have parallel walls.

4. The method of manufacture of claim 1, wherein the slots are cut such that the elongate members have parallel walls.

5. The method of manufacture of claim 1, wherein the tube comprises a flexible material.

6. The method of manufacture of claim 5, wherein the flexible material is Nitinol.

7. The method of manufacture of claim 1, wherein the shape-setting step comprises shape-setting a bend in the elongate members at a point proximate the proximal region.

8. The method of manufacture of claim 1, wherein the shape-setting step further comprises shape-setting a helical shape into the distal region of the elongate members.

* * * * *